(12) United States Patent
Speirs (10) Patent No.: US 6,434,796 B1
(45) Date of Patent: Aug. 20, 2002

(54) OXYGEN DELIVERY CANNULA RETAINER, CANNULA WITH RETAINERS ASSEMBLY, AND METHOD FOR RETAINING CANNULAS

(75) Inventor: Robert A. Speirs, West Valley City, UT (US)

(73) Assignees: Kathryn M. Speirs, Glendale, AZ (US); Paula J. Murphy; Randal A. Speirs, both of Murray, UT (US); Cynthia A. Billings, West Valley City, UT (US)

( * ) Notice: Subject to any disclaimer, the term of this patent is extended or adjusted under 35 U.S.C. 154(b) by 0 days.

(21) Appl. No.: 09/422,007

(22) Filed: Oct. 20, 1999

(51) Int. Cl.$^7$ ............................................... A44B 21/00
(52) U.S. Cl. .............................. 24/3.1; 24/336; 24/546; 24/373
(58) Field of Search ........................ 24/3.1, 3.11, 67 P, 24/336, 338, 546, 373, 374, 370, 129 R, 130, 462, 136 A, 115 A, 598.5, 598.6, 600.6, 601.7; 403/391, 389, 397

(56) References Cited

U.S. PATENT DOCUMENTS

| | | | | |
|---|---|---|---|---|
| 312,105 A | * | 2/1885 | Faivre | 24/373 |
| 1,027,041 A | * | 5/1912 | Gammelgaard | 24/374 X |
| 1,235,854 A | * | 8/1917 | Stapf | 24/373 |
| 1,746,942 A | * | 2/1930 | Hise | 24/370 |
| 2,664,899 A | * | 1/1954 | Attias | 24/336 X |
| 2,676,380 A | * | 4/1954 | Lindquist et al. | 24/601.7 |
| 3,122,803 A | * | 3/1964 | Boggess et al. | 24/373 |
| 3,432,129 A | * | 3/1969 | Santucci | 24/343 |
| 4,474,383 A | * | 10/1984 | Kikis | 24/336 X |
| 4,979,714 A | * | 12/1990 | Russsel et al. | 24/370 X |

* cited by examiner

Primary Examiner—Robert J. Sandy
(74) Attorney, Agent, or Firm—Mallinckrodt & Mallinckrodt (57) ABSTRACT

Cannula retainers for use with oxygen delivery cannulas having a tubular nose piece for introducing oxygen into a person's nose, dependent oxygen tubes extending from opposite ends thereof for looping over the person's ears and which terminate at a connector for connection to an main oxygen delivery tube, and a slidable retaining collar for tensioning the oxygen tubes against the person's lower jaw. The cannula retainers comprise a tubular, band, or elastic body having a hook, clip, loop, or tubular member connected to each end of the body for attachment to the upper and lower portions of the oxygen tube to retain the oxygen tube in a looped configuration about the person's ear. The cannula retainers can be of a fixed length or of a variable length such as being stretchable or elastic, or of an adjustable length. Cannula with retainer assemblies include any of the cannula retainers of the invention with such cannulas. The method of the invention is for retaining such cannulas to a person's head by retaining the upper and lower portions of the respective oxygen tubes in a predetermined spaced relationship ahead of the respective ear in a looped configuration about the person's ears such that pulling on the connector and lower portions of the oxygen tubes does not significantly add tension to the upper portions of the oxygen tubes so as to force the nose piece further into the person's nose causing discomfort. The method can include a further step of adjusting the length of the cannula retainers to fit the person's head.

6 Claims, 5 Drawing Sheets

OXYGEN DELIVERY CANNULA RETAINER, CANNULA WITH RETAINERS ASSEMBLY, AND METHOD FOR RETAINING CANNULAS

BACKGROUND OF THE INVENTION

1. Field

The invention is in the field of cannulas for attachment to a person's head to deliver oxygen through the person's nose from a pressurized oxygen tank or oxygen concentrator.

2. State of the Art

There are a number of persons whom require supplemental oxygen such as after surgery to aid in the healing process, and persons having lungs of limited capacity due to lung damage which require supplemental oxygen to assist in everyday life. Such damage to a person's lungs occurs by scarring of the lung tissue caused by irritants in the air such as tobacco smoke, asbestos particles, and chemicals, and by diseases such as lung cancer and emphysema.

Prior art cannulas for delivery of oxygen to the person's nose typically comprise a nose piece, a pair of oxygen tubes, an adjustment collar, and a connector. The nose piece has a tubular body with a pair of integral nostril tubes. A first end of each oxygen tube is attached to respective end portions of the nose piece. Second ends of each oxygen tube are attached to the connector. A mating connector attached to a main oxygen delivery tube connects to the connector of the cannula for delivery of oxygen from a compressed oxygen supply tank or from an oxygen concentrator which separates oxygen from the ambient air. The adjustment collar is slidable along the oxygen tubes to adjust the fit of the cannula to the person's head.

The prior art cannula fits around the person's head with the nostril tubes of the nose piece inserted into the respective nostrils of the person's nose to deliver oxygen thereto. The oxygen tubes are each looped over a respective ear of the person with an upper portion thereof closely adjacent a respective cheek bone of the person and lower portions thereof fitting adjacent respective lower side portions of the person's jaw. The adjustment collar is positioned just below the lower center portion of the person's jaw to provide tension on the oxygen tubes so as to retain the nose piece in position closely adjacent the person's nose and to retain the entire cannula in place on the person's head.

A major problem with such prior art cannula occurs when the main oxygen delivery tube which delivers oxygen to the cannula gets snagged on an object, which happens frequently during the course of a day for a mobile person such as when carrying or pulling a portable oxygen tank or a person connected by a long main tube to a stationary oxygen concentrator located in a house or apartment. When such snagging occurs, the oxygen tubes are typically pulled generally downwardly such that the tension on the upper portions of the oxygen tubes is significantly increased jamming the nose piece into the person's nose causing much discomfort to such person and potential injury to the nose, ears, and face of the person. Such snagging also causes the upper portions of the respective oxygen tubes to move upwardly towards the person's eyes partially blocking the field of view, which can be particularly hazardous while driving an automobile.

Another problem is that the retaining collars are prone to slip downwardly during cannula use such that the tension on the oxygen tubes is reduced. Such loss of tension can cause the nose piece to fall from the person's nose and the oxygen tubes to fall from around the person's ears. This is particularly prone to occur when the person is asleep and is typically caused by tossing and turning of the person causing contact of the cannula and retaining collar against the bed. The person generally awakes when the nose piece dislodges or falls from the person's nose due to the insufficient supply of oxygen to the person's brain, and the person must subsequently reattach the cannula. This activity disrupts the person's sleep particularly when occurring multiple times each night. If the person does not awake, potentially serious hypoxia, including permanent brain damage and death can occur due to the lack of sufficient oxygen supply to the person's brain.

There is a need for a means and method for retaining a cannula in place during use, particularly while the person is asleep, and for preventing painful tugging on the oxygen tubes jamming the nose piece into the person's nose, particularly while the person is awake and active. Likewise, there is a need for an improved cannula using such means.

SUMMARY OF THE INVENTION

The invention comprises cannula retainers, cannula with retainer assemblies which include such cannula retainers, and methods of use of such cannula with retainer assemblies. The cannula retainers are for use with any of a number of standard type cannulas commercially available of the type having a tubular nose piece with nostril tubes for introducing oxygen into a person's nose, dependent oxygen tubes extending from opposite ends of the nose piece for looping over the person's ears forming upper and lower oxygen tube portions the lower portions of which terminate at a connector for connection to a mating connector attached to an oxygen main tube for delivery of oxygen, and typically including a slidable retaining collar disposed about the lower portion of the oxygen tubes for tensioning the oxygen tubes against the person's lower jaw.

The cannula retainers comprise an elongate body means having opposite end portions and a pair of retaining means, one connected to each of the opposite end portions of the body means for attachment to respective upper and lower portions of the oxygen tube to retain the oxygen tube in a looped configuration about the person's ears. The cannula retainers can be of a fixed length or of a variable length including being stretchable or elastic and of an adjustable length.

A first embodiment of the cannula retainer is of fixed length, with a first version thereof comprising an elongate, resilient, discontinuous band, wherein the body means comprises a middle portion of the band and the retaining means comprises the end portions of the band which form end clips having respective loops, with the respective ends of the band spaced apart and angled outwardly from the body means to aid in insertion of the oxygen tube into the end clips. A second version, fixed length cannula retainer comprises an elongate, resilient, continuous band wherein the body means comprises a middle portion of the band with opposite band portions juxtaposed and the retaining means comprises end portions of the band which are doubled over to form end loops. A third version, fixed length cannula retainer comprises an elongate, resilient, discontinuous band wherein the body means comprises a middle portion of the band and the retaining means comprises end portions of the band which are doubled over to form end loops, wherein the ends of the band overlap, and a slidable tubular buckle fits over the middle portion of the band and over the ends of the band to retain the respective ends to the middle portion of the band.

A fourth version, fixed length cannula retainer has a body means which comprises an elongate tubular member having opposite ends and the retaining means which comprises a pair of locking belt loops each having a locking body with a resilient ratchet tooth therein and an integral locking belt which extends from the locking body having a plurality of transverse teeth, each locking body being affixed within a respective end of said tubular member such that said locking belt is insertable into a hole therein so as to form a loop to receive oxygen tube. with the ratchet tooth retaining the locking belt therein. A fifth version, fixed length cannula retainer has a body means which comprises an elongate tubular body and the retaining means which comprises a pair of T-shaped tubular members affixed to opposite ends thereof into which a respective oxygen tube fits.

A second embodiment of the cannula retainer is of variable length, with a first version wherein the body means comprises an elongate body member which is made of a stretchable, elastic material and wherein the retaining means comprises a pair of hook members affixed to opposite ends thereof. A second version, variable length cannula retainer has a body means which comprises a tubular member which is internally threaded at the respective ends thereof and the retaining means which comprises a pair of hook members each having a hook portion and an externally threaded shaft each of which threads into a respective end of the tubular member. The variable length is achieved by rotating the tubular member relative to the hook members. Respective pairs of ends of the tubular member and the threaded shafts are preferably threaded in opposite right-hand and left-hand directions such that rotational movement of the tubular member relative to the hook members moves both of the hook members in linearly opposite directions so as to simultaneously lengthen or shorten the cannula retainer. A third version, variable length cannula retainer is similar to the second version, except that the hook members are replaced by clip members each having a clip and an externally threaded shaft which threads into a respective end of the tubular member. The operation thereof is the same as the second version. A fourth version, variable length cannula retainer includes a body means such as comprising a tubular body, a retaining means such as comprising a pair of elongate members which fit within respective bores in the ends of the tubular body, and a frictional means such as comprising a plurality of ribs on the respective elongate members and inside the respective bores which interlock so as to retain the respective retaining means in a fixed position until application of a linear force between the respective retaining means and the body means sufficient to overcome the frictional means.

The cannula with retainer assemblies of the invention comprise a tubular nose piece having a pair of nostril tubes for introducing oxygen into the nostrils of the person's nose., a pair of dependent oxygen tubes extending from opposite ends of the nose piece for looping over the ears of the a user forming upper and lower oxygen tube portions, a connector connected to opposite end portions of the oxygen tubes for connection to the mating connector on the main tube, a slidable retaining collar or similar means disposed about the respective lower portions of the oxygen tubes for tightening below a user's chin, and a pair of fixed length or variable length cannula retainers each being for attachment to the upper and lower portions of a respective oxygen tube to retain the oxygen tube in a looped configuration about the person's ears.

The method of the invention is for retaining a cannula of the type described above to a person's head, comprising the step of retaining the upper and lower portions of the respective oxygen tubes in a predetermined spaced relationship forward of the person's respective ear in a looped configuration about the user's ear such that sufficient tension is maintained on the nose piece during cannula use to maintain the nose piece in the proper oxygen delivery position and wherein pulling downwardly on the connector and lower portions of the oxygen tubes does not significantly add tension to the upper portions of the oxygen tubes so as to uncomfortably force the nose piece further into the person's nose. The method can be practiced using any-of the cannula retainers of the invention, fixed length or variable length. The method can include a further step of adjusting the length of the cannula retainers to fit the person's head.

THE DRAWINGS

The best mode presently contemplated for carrying out the invention is illustrated in the accompanying drawings, in which.

DETAILED DESCRIPTION OF THE ILLUSTRATED EMBODIMENTS

Figure 1:
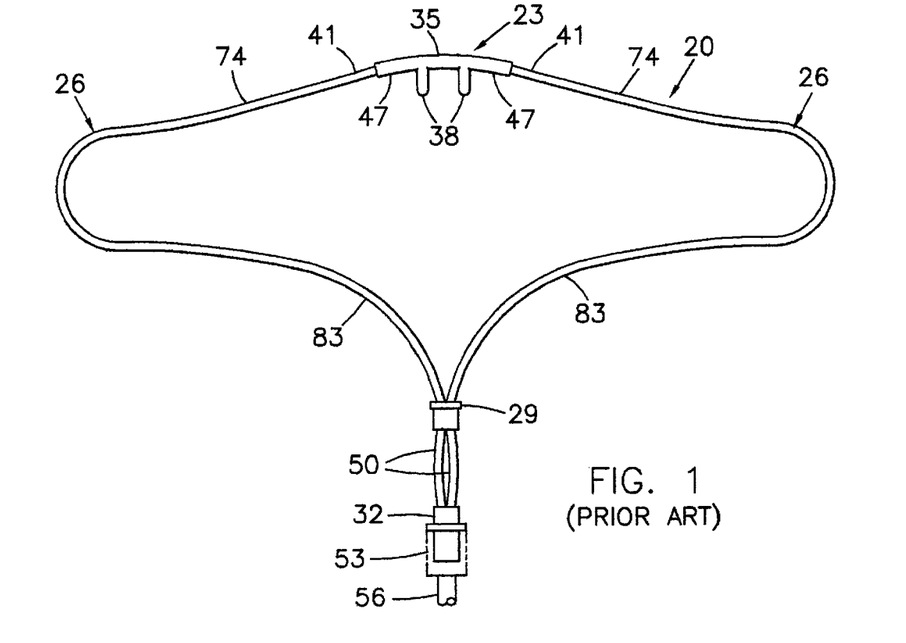
FIG. 1 is a top plan view of a typical prior art cannula.

Referring to FIG. 1 therein is shown a prior art cannula 20 which comprises a nose piece 23, a pair of oxygen tubes 26, an adjustment collar 29, and a tubular male connector half 32. Nose piece 23 has a tubular body 35 with a pair of integral nostril tubes 38 in fluid communication therewith which extend normally therefrom. A first end 41 of each oxygen tube 26 is affixed within respective end portions 44 and 47 of nose piece 23. Second ends 50 of each oxygen tube 26 are affixed to male connector half 32. A female connector half 53 with an attached oxygen delivery main tube 56, shown in dotted lines, slidably connects to male connector half 32 for delivery of oxygen from a supply tank or oxygen concentrator (not shown) through main tube 56. Adjustment collar 29 is slidable along oxygen tubes 26.

Figure 2:
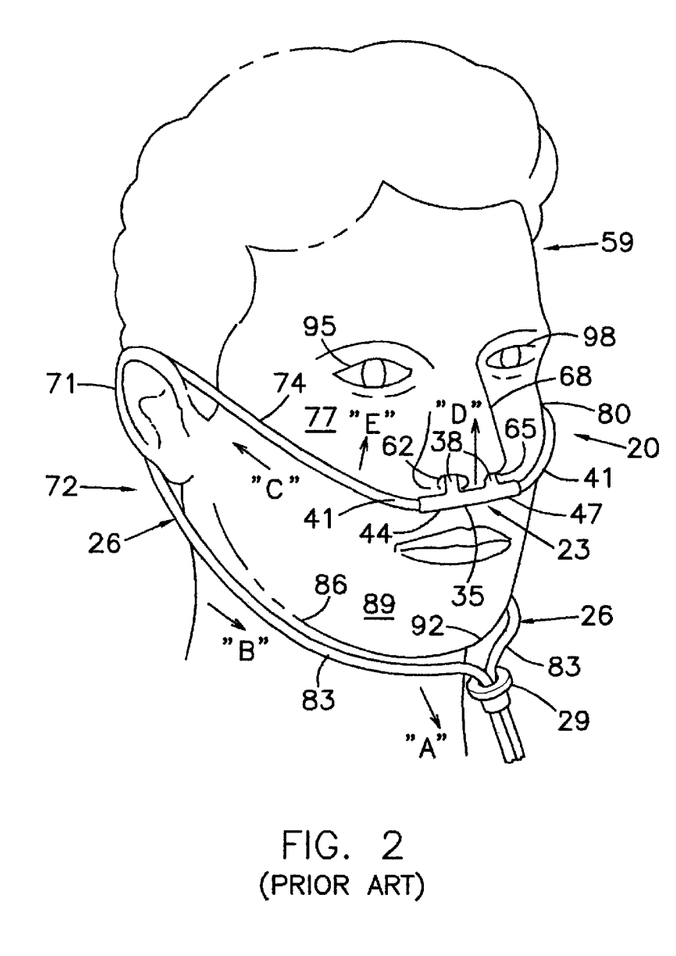
FIG. 2, a right side perspective view of a such prior art cannula as used by a person.

Shown in FIG. 2 is prior art cannula 20 as attached for use to the head 59 of a person to whom oxygen is to be delivered. Cannula 20 fits around the person's head 59 with nostril tubes 38 of nose piece 23 inserted into respective nostrils 62 and 65 of the person's nose 68 to deliver oxygen thereinto. Oxygen tubes 26 each loop over an ear such as ear 71 forming a loose loop 72 with an upper portion 74 of each oxygen tube 26 juxtaposed a respective cheek bone 77 and 80 and lower portions 83 thereof fitting adjacent respective lower side portions such as lower side portion 86 of the person's lower jaw 89. Adjustment collar 29 is positioned just below a lower center portion 92 of the person's jaw 89 to retain cannula 20 in place on the person's head 59. A major problem with such prior art cannula 20 is when main tube 56 gets snagged on an object (not shown) which occurs frequently during the course of a day for a mobile person such as carrying or pulling a portable oxygen tank (not shown) or a person connected by a long main tube to an oxygen concentrator located in a house or apartment. When such snag occurs, oxygen tubes 26 are typically pulled downwardly as at arrow "A" which pulls lower portions 83 thereof as at arrow "B" causing pressure on the person's ears such as ear 71 and tension in oxygen tubes 26 which slides upper portions 74 of respective oxygen tubes 26 around the person's ears such as ear 71 as at arrow "C" causing nose piece 23 to move upwardly as at arrow "D" jamming against the person's nose 68 causing discomfort and possible injury thereto. Likewise, such snagging causes upper portions 74 of the respective oxygen tubes 26 to move upwardly as at arrow "E" towards the person's eyes 95 and 98 partially blocking the field of view, which can be hazardous such as when driving an automobile.

Figure 3:
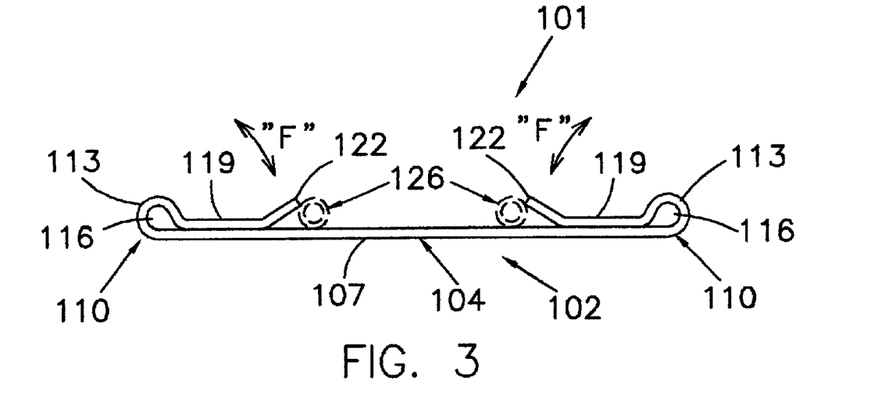
FIG. 3, a side elevational view of a first version, first embodiment, fixed length cannula retainer of the invention having a discontinuous band and a pair of integral end clips.

Referring to FIG. 3, therein is shown a first version of a first embodiment, fixed length cannula retainer 101 comprising an elongate, discontinuous resilient plastic or metal band 104 wherein the body means comprises an elongate center portion 107 of band 104 and the retaining means comprises a pair of integral end clips 110. Each end clip 110 comprises a doubled over portion of band 104 forming a loop 113 defining a hole 116 of such size as to firmly grip an oxygen tube 26, shown in dotted lines, when placed therein. Ends 119 of band 110 extend from respective loops 113 of clips 110 and terminate in an angled upstanding guiding portion 122. Ends 119 can be deflected outwardly as at arrows "F" by pushing oxygen tubes 26 against respective guiding portions 122 until oxygen tube 26 seats within respective holes 116 wherein clip 110 returns to the undeflected position shown.

Figure 4:
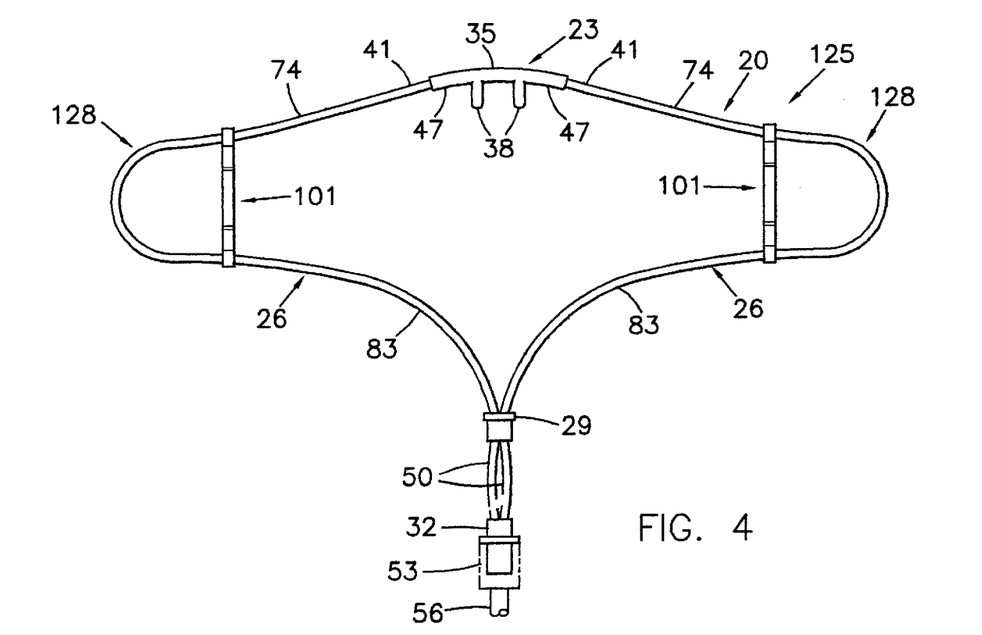
FIG. 4, a top plan view of such prior art cannula with a pair of such first version, fixed length cannula retainers attached thereto comprising a first version cannula with retainer assembly.

In FIG. 4 is shown a pair of the fixed length cannula retainers 101 as installed on prior art cannula 20 so as to comprise a first version cannula with retainer assembly 125. Cannula with retainer assembly 125 comprises nose piece 23, a pair of dependent oxygen tubes 26, adjustment collar 29, tubular male connector half 32, and a pair of the fixed length cannula retainers 101. Each cannula retainer 101 attaches to an upper portion 74 and to a lower portion 83 of a respective oxygen tube 26 so as to form respective tight loops 128.

Figure 5:
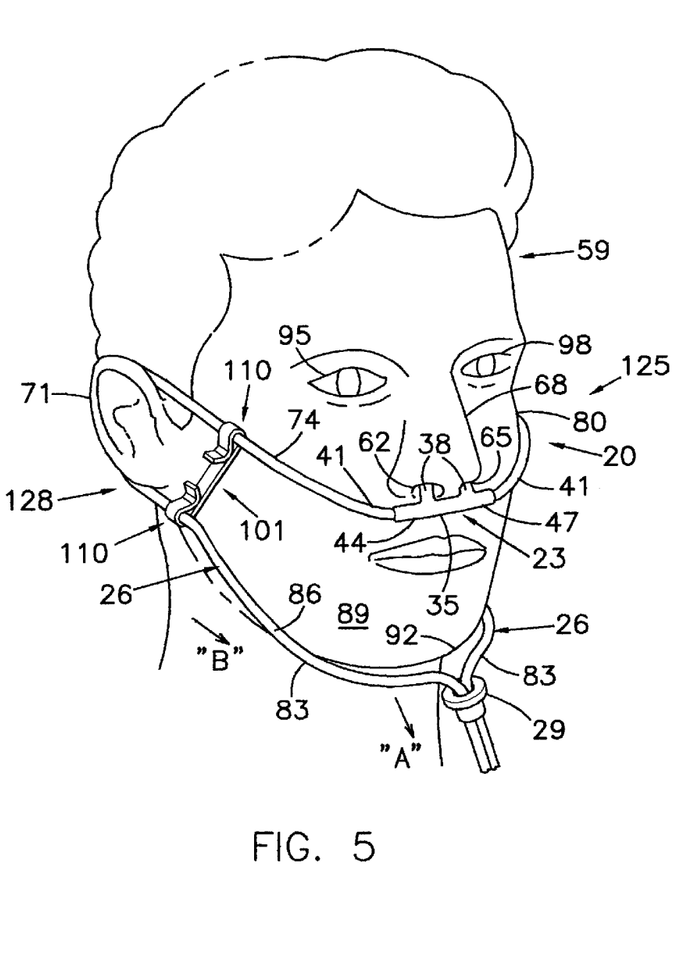
FIG. 5, a right side perspective view of such first version cannula with retainer assembly as used by a person.

Referring to FIG. 5, therein is shown cannula with retainer assembly 125 as attached to the person's head 59 for delivery of oxygen to the person's nose 68 in a similar manner to cannula 20 alone. Tight loop 128 is formed around the person's ears 71 which prevents oxygen tubes 26 from sliding around the person's ears such as ear 71. Therefore, when main tube 56 gets snagged on an object such that oxygen tubes 26 are typically pulled downwardly as at arrow "A" which pulls lower portions 83 thereof as at arrow "B", the tight loops 128 in the oxygen tubes 26 formed by respective fixed length cannula retainers 101 prevent oxygen tubes 26 from sliding around the person's ears such as ear 71. Therefore, most of the tension in lower portions 83 of oxygen tubes 26 is confined to lower portions 83 thereof pulling on the person's ears such as ear 71 rather than being transmitted through respective upper portions 74 thereof and causing nose piece 23 to move upwardly and jamming against the person's nose 68 causing discomfort and possible injury thereto. Likewise, such snagging does not cause upper portions 74 of the respective oxygen tubes 26 to move upwardly towards the person's respective eyes 95 and 98 and partially block the person's field of view.

Figure 6:
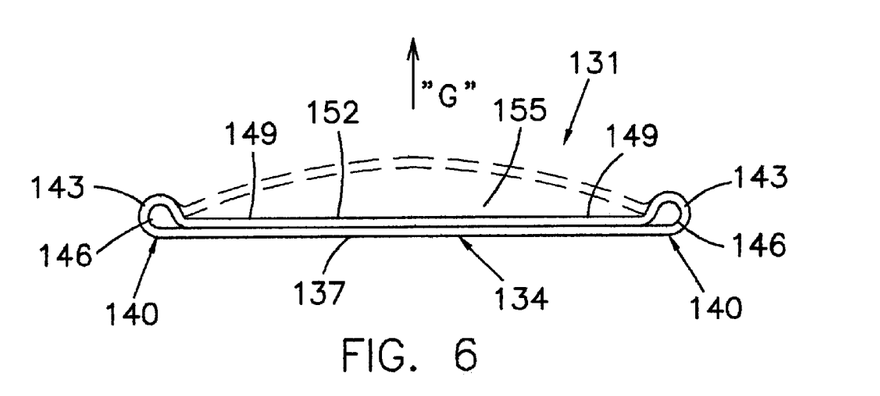
FIG. 6, a side elevational view of a second version, fixed length cannula retainer having a continuous band with integral end loops wherein the band deflects for installation to a cannula.

In FIG. 6 is shown a second version, fixed length cannula retainer 131 comprising an elongate, resilient plastic or metal continuous band 134 wherein the body means comprises an elongate center portion 137 of band 134 and the retaining means comprises a pair of integral end clips 140. Each end clip 140 comprises a doubled over portion of band 134 forming loop 143 defining a hole 146 of such size as to firmly grip an oxygen tube 26 when placed therein. Ends 149 of band 134 extend from respective loops 143 of clips 140 which join together to form an outer center portion 152 of band 134. Cannula retainer 131 attaches to cannula 20 by deflecting outer center portion 152 of band 134 outwardly (dotted lines) as shown by arrow "G" forming an opening 155 which connects to respective holes 146. An oxygen tube (not shown) is attached to cannula retainer 131 by forming the oxygen tube into a loop (not shown) and inserting the loop through opening 155 at the desired position to form the desired size loop with upper and lower portions 74 and 86 thereof seating in respective openings 146 and allowing outer center portion 152 to move back to the original position.

Figure 7:
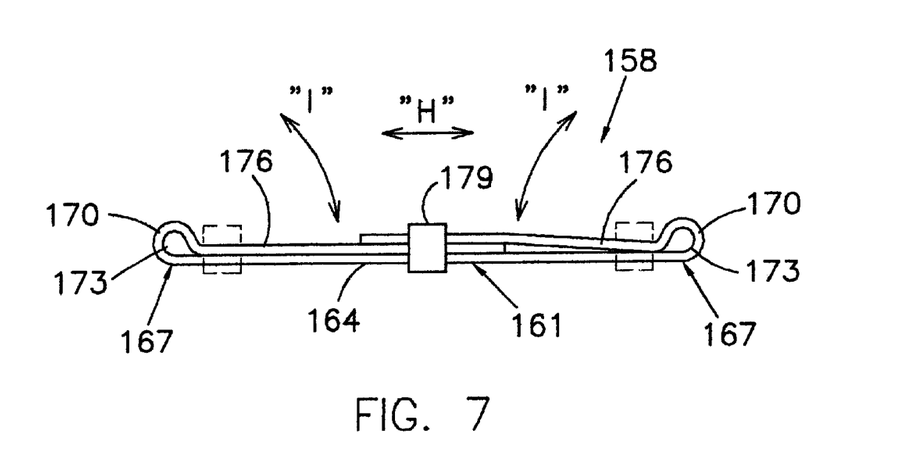
FIG. 7, a side elevational view of a third version, fixed length cannula retainer having a; discontinuous band with a pair of integral end clips, overlapping band ends, and a sliding retainer buckle.

Referring to FIG. 7, therein is shown a third version, fixed length cannula retainer 158 having a resilient plastic or metal band 161 wherein the body means comprises an elongate center portion 164 of band 161 and the retaining means comprises a pair of integral end clips 167. Each end clip 167 comprises a doubled over portion of band 161 forming a loop 170 defining a hole 173 of such size as to firmly grip an oxygen tube 26 when placed therein. Ends 176 of band 161 extend from respective loops 170 of end clips 167 with one overlapping the other. A tubular buckle 179 is disposed about center portion 164 of band 161 and ends 176 of end clips 167. Buckle 179 slides along center portion 164 of body 161 as at arrows "H" with loops 170 acting as stops to retain buckle 179 on band 161. By alternately sliding buckle 179 to respective positions adjacent respective loops 170 (dotted lines), inwardly extending portions 176 can be moved outwardly as at arrows "I" to allow the oxygen tubes (not shown) to seat within respective holes 173, and end clip 167 then can be returned to the undeflected position wherein buckle 179 can be moved back to the center position shown to retain both ends 176.

Figure 8:
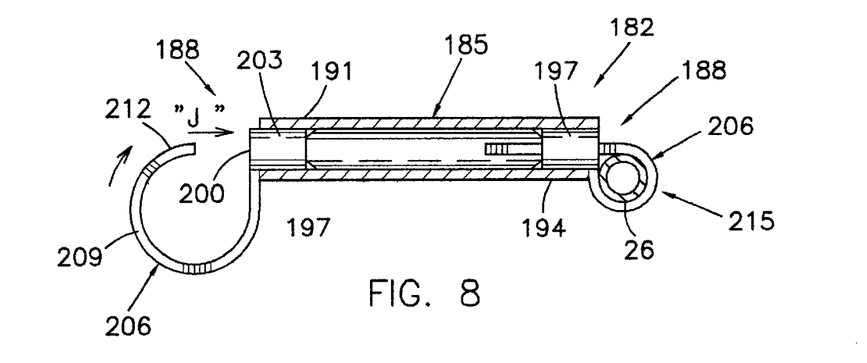
FIG. 8, a partial longitudinal sectional view of a fourth version, fixed length cannula retainer having a tubular body and a pair of locking belt loops, one belt loop shown in the open position and one shown as attached around an oxygen tube of a cannula.

In FIG. 8 is shown a fourth version, fixed length cannula retainer 182 having a body means which comprises an elongate plastic or metal tubular body 185 and a retaining means which comprises a pair of plastic cord ties or locking belt loops 188 affixed within respective opposite ends 191 and 194 of tubular body 185. Each locking belt loop 188 includes a locking body 197 having a rectangular hole 200 therethrough with a resilient ratchet locking tooth 203 therein. An integral locking belt 206 laterally extends from locking body 197 having an outer surface with a plurality of transverse teeth 212. Locking belt 206 is inserted into hole 200 as at arrows "J" to. form a loop 215 to receive oxygen tube 26 with ratchet tooth 203 being deflected by teeth 212 during insertion of locking belt 206 into hole 200 preventing removal of locking belt 206 from hole 200.

Figure 9:
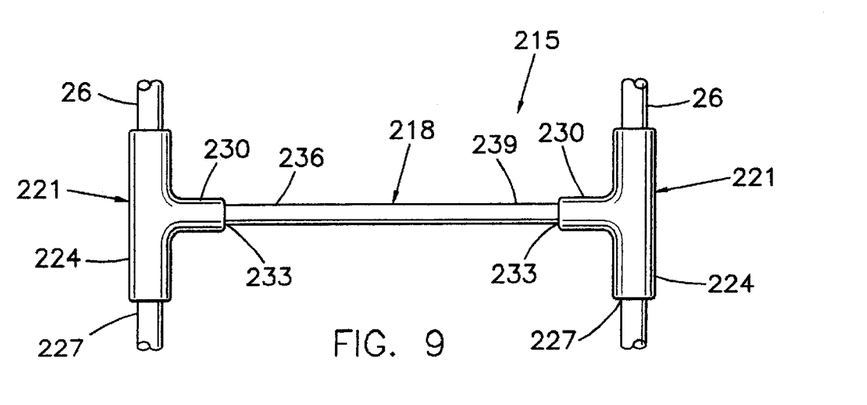
FIG. 9, a fragmentary top plan view of a fifth version, fixed length cannula retainer having a tubular body interconnecting a pair of T-shaped tubular members shown as attached to a pair of oxygen tubes of a cannula.

In FIG. 9 is shown a fifth version, fixed length cannula retainer 215 having a body means which comprises an elongate plastic tube 218 and a retaining means which comprises a pair of plastic T-shaped tubular connectors 221. Each tubular connector 221 comprises a tubular body portion 224 having a longitudinal hole 227 therethrough being of such inner diameter as to closely fit about a respective oxygen tube 26 so as provide frictional resistance to movement therebetween. A tubular leg portion 230 extends normally from body portion 224 and includes a hole 233. opposite ends 236 and 239 of tube 218 extend into holes 233 of leg portions 230 of respective tubular connectors 221 and are affixed therein such as by adhesively affixing or other such means.

Figure 10:
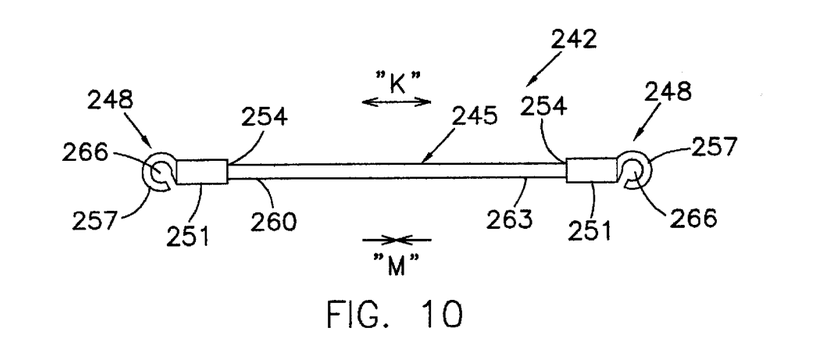
FIG. 10, a side elevational view of a first version, second embodiment, variable length cannula retainer having an elastic body and a pair offend hook members.

Referring to FIG. 10, therein is shown a first version, second embodiment, variable length cannula retainer 242 having a body means which comprises an elongate elastic band 245 such as of rubber and a retaining means which comprises a pair of plastic or metal end hook members 248. Each end hook member 248 comprises a body 251 having a longitudinal bore 254 which extends thereinto and a hook portion 257. Opposite ends 260 and 263 of elastic band 245 extend into bores 254 of respective hook members 248 and are affixed therein such as by crimping body 251 therearound, adhesively affixing, or other such means. The diameter of an opening 266 of hook portion 257 is of such size as to firmly grip an oxygen tube 26 placed therein. Elastic band 245 allows hook members 248 to move as at arrows "K" to absorb tensile and other forces from oxygen tubes 26 during use for added user comfort.

Figure 11:
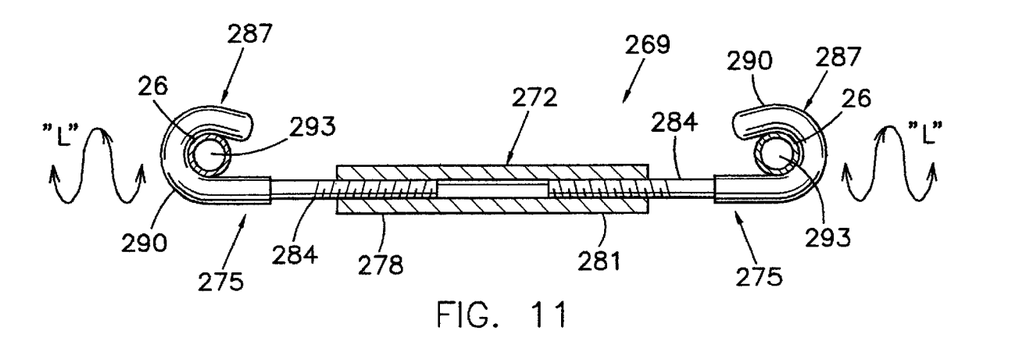
FIG. 11, a partial longitudinal sectional view of a second version, variable length cannula retainer which operates rotationally and which includes a pair of rubberized end hook members, shown as attached to a pair of oxygen tubes of a cannula.

In FIG. 11 is shown a second version, variable length cannula retainer 269 having a body means which comprises an elongate plastic or metal tubular body 272 and a retaining means which comprises a pair of plastic or metal hook members 275. Opposite end portions 278 and 281 of tubular body 272 are internally threaded. Each hook member 275 comprises an externally threaded shaft 284 and a hook portion 287 with a rubberized or vinyl dip cover 290. Hook members 275 thread into and out of end portions 278 and 281 as at arrows "L" to adjust the length of cannula retainer 269, which directions of threading can be made right hand for one and left hand for the other for operation of simultaneously extending and retracting both hook members 275 by rotating tubular body 272. The diameter of an opening 293 of hook portion 287 is of such size as to firmly grip an oxygen tube 26 therein with cover 290 adding frictional resistance to movement.

Figure 12:
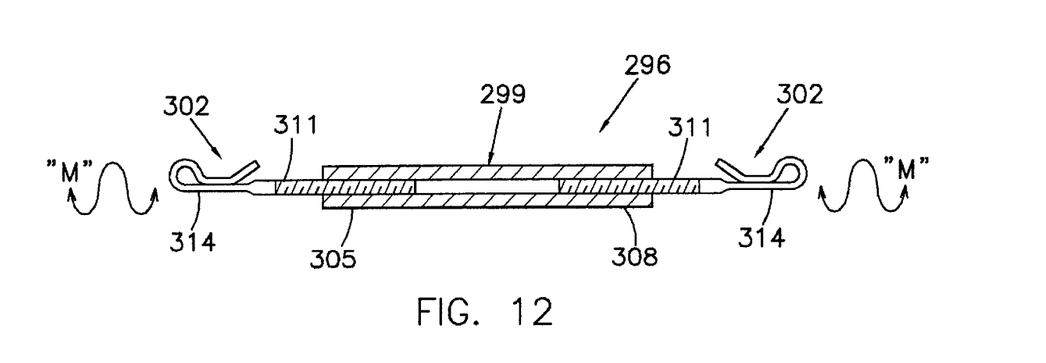
FIG. 12, a partial longitudinal sectional view of a third version, variable length cannula retainer which is operates rotationally and which includes a pair of end clips.

In FIG. 12 is shown a third version, variable length cannula retainer 296 having a body means which comprises an elongate plastic or metal tubular body 299 and a retaining means which comprises a pair of plastic or metal end clip members 302. Opposite end portions 305 and 308 of tubular body 299 are internally threaded. Each end clip member 302 comprises an externally threaded shaft 311 and an integral end clip 314 of similar construction and operation as end clip 110 of first version, fixed length cannula retainer 101 to receive oxygen tube 26 (FIG. 3). Clip members 302 thread into and out of threaded end portions 305 and 308 as at arrows "M" to adjust the length of cannula retainer 296, which directions of threading can likewise be made right hand for one and left hand for the other for operation of simultaneously extending and retracting both end clip members 302 by rotating tubular body 299.

Figure 13:
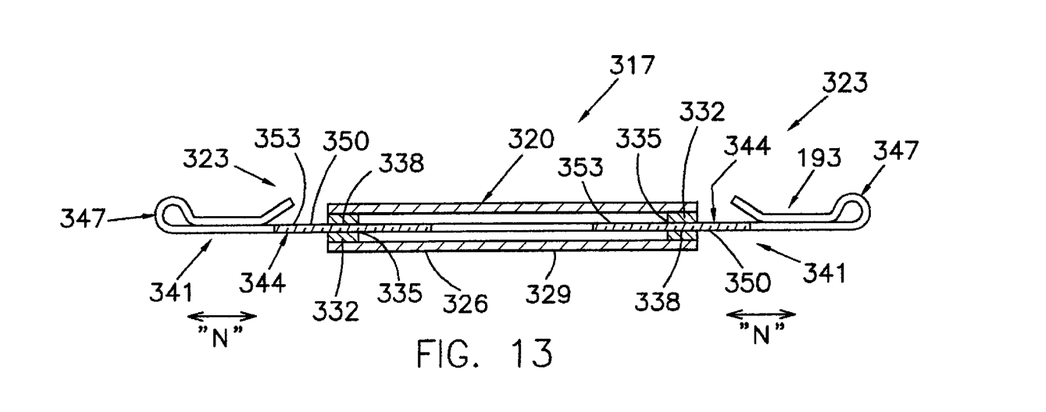
FIG. 13, a partial longitudinal sectional view of a fourth version, variable length cannula retainer which has a tubular body into which a pair of end clips linearly slide being frictionally retained therein.

In FIG. 13 is shown a fourth version, variable length cannula retainer 317 having a body means which comprises an elongate plastic or metal tubular body 320 and a retaining means which comprises a pair of two-piece locking belt assemblies 323 affixed in opposite ends 326 and 329 thereof. Each locking belt assembly 323 includes a locking body 332 having a rectangular hole 335 therethrough with a plurality of transverse locking teeth 338 therein. A locking belt 341 of locking belt assembly 323 has a belt portion 344 which extends into hole 335 of locking body 332 as at arrows "N" and an integral end clip 347 of similar construction and operation as end clip 110 of first version, fixed length cannula retainer 101 to receive a respective oxygen tube 26 (FIG. 3). Locking belt 341 has an outer surface 350 having a plurality of transverse teeth 353 and is inserted into hole 335 as at arrows "N" with locking teeth 353 thereof contacting locking teeth 338 of locking body 332 upon insertion of locking belt 341 into hole 335 providing resistance to movement in both longitudinal directions of locking belt 341 in hole 335 yet still allowing movement for adjustment of the length of cannula retainer 317.

Many variations of the cannula retainers of the invention are possible without departing from the overall inventive concept thereof. For example, the lengths of the cannula retainers can be made to suit the person using the cannula retainer such as adult sizes, child sizes, and even sizes to suit infants. Such sizes can be of fixed length or variable length. The versions which use frictional means such as locking teeth can be made to unidirectionally permanently lock if desired. Such frictional means can be accomplished without locking teeth such as wherein a spring member or resilient member such as made of rubber rubs against the band to provide frictional resistance. The body means and retaining means can comprise a single elastic band which extends around the respective upper and lower portions of the oxygen tube. Separate retaining means such as clips, hooks, loops, and tubes can be affixed to the body means such as by rivets, screws or bolts, adhesives, or such as in the case of an elastic body made of an elasticized cloth material by sewing. The elastic body means can comprise molded rubber and the retaining means comprise integrally molded rubber loops. The cannula retainers can be removable or integrally manufactured with the cannula so as not to be removable. The cannula retainers can be made of plastics such as polypropylene, nylon, or other suitable plastic material in any color desired, including color coded sizes for adults, children, and infants, or from other suitable materials such as stainless steel, spring steel, or other metal, with the elastic versions being made of rubber or compounds - thereof, or other suitable elastomeric material. The externally threaded rods of the hook member or the clip and internally threaded ends of the tubular member can be reversed such that the tubular member is a solid member with externally threaded ends and the externally threaded rods replaced by internally threaded rods. The cannula retainer and the cannula with retainer assemblies of the invention also are also usable wherein the respective lower portions of the oxygen tubes curve rearwardly, from the lower attachment point of the respective cannula retainer to the respective oxygen tube, toward the back of the person rather than downwardly to the front of the person.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A cannula retainer for use with a cannula of the type having a tubular nose piece with nostril tubes for introducing oxygen into a user's nose, dependent oxygen tubes extending from opposite ends of the nose piece for looping over the ears of the a person forming upper and lower oxygen tube portions and which lower portions of the oxygen tubes extend to a connector for connection to a mating connector attached to an oxygen main tube for delivery of oxygen, and a slidable retaining collar disposed about the lower portion of the air tubes for tightening against the person's lower jaw, comprising:

a body having opposite end portions; and a resilient retaining device connected to each of said opposite end portions of said body and defining a substantially circular hole at each of said opposite end portions of such size as to firmly grip one of the oxygen tubes when placed therein, said retaining device being deflectable to open said holes to facilitate attachment to the upper and lower portions of one of the oxygen tubes and which returns to an undeflected position to firmly grip and retain the oxygen tube in a looped configuration about one of the person's ears.

2. A cannula retainer according to claim 1, wherein the retaining device comprises a pair of end clips which are integral with the body, each of said end clips having a doubled over portion forming a loop defining the hole to firmly grip one of the oxygen tubes in the undeflected position when placed therein, and respective ends of said end clips being juxtaposed said body in the undeflected position.

3. A cannula retainer according to claim 2 which is of a fixed length.

4. A cannula retainer according to claim 3, comprising a resilient, narrow, discontinuous band wherein the body comprises a middle portion thereof and end portions thereof each forming one of the end clips.

5. A cannula retainer according to claim 4, wherein respective ends of the band are spaced apart and angled outwardly from the body forming respective angled upstanding guiding portions at each clip which can be deflected outwardly to open each of said clips by pushing one of the oxygen tubes thereagainst until the oxygen tube seats within one of the holes of said clip, which clip subsequently returns to the undeflected position to grip the oxygen tube.

6. A cannula retainer according to claim 4, wherein respective ends of the band overlap and are juxtaposed the body in respective undeflected positions and a slidable tubular buckle fits thereover in a center position to retain said ends juxtaposed said body, and wherein by alternately sliding said buckle to a position adjacent one of the loops permits moving the end clip opposite thereof into the deflected position to permit the oxygen tube to be seated within the hole of said clip, and the end clip can then be returned to the undeflected position wherein said buckle can be moved back to the center position to retain both of said ends.

* * * * *